United States Patent [19]

Quirk et al.

[11] Patent Number: 4,668,812

[45] Date of Patent: May 26, 1987

[54] PROCESS FOR THE PREPARATION OF OLEFINIC SILANES AND SILOXANES

[75] Inventors: Jennifer M. Quirk, College Park, Md.; Bernard Kanner, West Nyack, N.Y.

[73] Assignee: Union Carbide Corporation, Danbury, Conn.

[21] Appl. No.: 815,003

[22] Filed: Dec. 31, 1985

[51] Int. Cl.$^4$ ................................................ C07F 7/08
[52] U.S. Cl. ...................................... 556/466; 556/467
[58] Field of Search ................................ 556/466, 467

[56] References Cited

U.S. PATENT DOCUMENTS

| 2,682,512 | 6/1954 | Agre | 556/466 X |
| 3,198,766 | 8/1965 | Nitzsche et al. | 260/46.5 |
| 3,595,733 | 7/1971 | Ching et al. | 260/448.2 E |
| 3,666,783 | 5/1972 | LeFort | 556/467 X |

FOREIGN PATENT DOCUMENTS

| 0025540 | 2/1981 | Japan | 556/466 UX |
| 1365431 | 9/1974 | United Kingdom | 556/466 UX |

OTHER PUBLICATIONS

"J. Org. Chem.", 1984, 49, pp. 3389-3392.
"Angew. Chem. Int. Ed. Engl.", 19, 1980, p. 928.
"Chem. Abs.", 98, 1983, p. 658.
"J. of Molecular Catalysis", 26, 1984, pp. 89-104.
"J.C.S. Chem. Comm.", 1981, pp. 673-674.
"J. Org. Chem.", 48, 1983, pp. 5101-5105.
"J. Organomet. Chem.", 253, 1983, pp. 349-362.
"J. Organomet. Chem.", 128, 1977, pp. 345-358.
"J.C.S., Chem. Comm.", 1983, p. 1193.
"J.C.S.", 1980, pp. 308-312.
"Czechoslov. Chem. Commun.", 40, 1975, pp. 3680-3687.
"Tetrahedron", 18, 1962, pp. 61-68.

Primary Examiner—Paul F. Shaver
Attorney, Agent, or Firm—Steven H. Flynn

[57] ABSTRACT

A novel synthesis for silanes and siloxanes containing olefinic bonds wherein an aminosilane, siloxane alkoxysilane or alkylalkoxysilane and an olefin undergo a dehydrocondensation in the presence of a rhodium or ruthenium catalyst.

21 Claims, No Drawings

PROCESS FOR THE PREPARATION OF OLEFINIC SILANES AND SILOXANES

BACKGROUND OF THE INVENTION

1. Field of the Invention

The present invention generally relates to a novel process for the synthesis of olefinic silanes and/or siloxanes. More particularly, the process provides the dehydrocondensation of a silicon-containing compound with an olefin in the presence of a rhodium or ruthenium catalyst in a one-step process.

2. Prior Art

The hydrosilation reaction was discovered in 1947 and over the years has become one of the best known and most widely practiced reactions in organosilicon chemistry, including its use in a wide variety of large scale commercial applications. It has also been the subject of several extensive reviews, see for instance: *Organic Insertion Reactions of Group II Elements*, Consultants Bureau, NY, 1966; *Organometallic Compounds of the Group IV Elements*, Deckker, NY, 1968, Vol. I; *Preparation of Carbofunctional Organosilanes By An Addition Reaction*, Moscow, 1971; Russ. Chem. Rev. 46, 264 (1977); and J. Organometal. Chem. Library 5, 1977, pg 1–179.

The hydrosilation reaction between a silane and an olefin is generally depicted as follows:

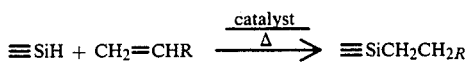

In operating a hydrosilation reaction, various transition metals are known to be effective catalysts. U.S. Pat. No. 2,823,218 teaches chloroplatinic acid, a soluble form of platinum, as a particularly effective hydrosilation catalyst.

The literature has also disclosed dehydrocondensation (also known as dehydrogenative silylation) between silanes and olefins. This reaction is depicted as follows:

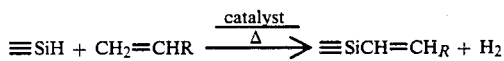

In U.S. Pat. No. 3,595,733 osmium compounds, such as chloroosmic acid, was taught as being capable of catalyzing this dehydrocondensation reaction. However, osmium compounds are very expensive and thus other routes have been explored, such as in British Pat. No. 1,365,431 where nickel complexes are disclosed as catalyzing the reaction of ≡SiH compounds with olefins to provide organosilicon compounds having olefinic unsaturation.

More recently, rhodium and ruthenium have been suggested as a possible dehydrocondensation catalyst.

In JP No. 57,140,788 2-(perfluorohydrocarbyl) vinyl silanes were prepared by the reaction of ≡SiH with perfluorohydrocarbyl—containing olefins in the presence of rhodium or ruthenium catalyst complexes.

It has been suggested in the literature that triethylsilane undergoes a dehydrocondensation reaction instead of hydrosilation with olefins such as styrene of 1-decene using RhCl(PPh$_3$)$_3$ or Ru$_3$(OH)$_{12}$ as a catalyst, J. Org. Chem. 1984, 49, 3389–3392.

Ru$_3$(CO)$_{12}$ was reported to catalyze a dehydrocondensation reaction between simple silanes and olefins in Angew. Chem. Int. Ed. Engl. 19 (1980) 928.

Rhodium catalysts were unexpectedly found to yield E-hex-1-en-1-yl(triethyl)silane and E-hex-2-en-1-yl(triethyl)silane when triethylsilane and hex-1-ene were reacted together in Journal of Molecular Catalysis, 26 (1984) 89–104.

The reaction of simple silanes, including triethoxysilane, with an olefin in the presence of a rhodium catalyst was found to generate β-silyl-substituted trans-styrenes. In this reaction, excess styrene was employed and selectivity was reportedly enhanced by placing bulky substituents on the silanes. J. Organomet. Chem. 1983, 48, 5101–5105.

Finally, ruthenium phosphine complexes were reported to generate trace amounts of unsaturated product when the reactants were alkoxysilanes and olefins. J. Organomet. Chem., 253 (1983) 349–362.

Although these references generally teach the dehydrocondensation between simple silanes and olefins in the presence of a rhodium or ruthenium catalyst, it is unexpected that this reaction would take place with the more complex secondary aminosilanes, siloxanes, alkoxysilanes and alkylalkoxysilanes.

OBJECTIVES OF THE INVENTION

The objective of the present invention is to provide a one-step process which will synthesize olefinic silanes and/or siloxanes.

Another objective of the present invention is to arrive at a process which has yields that are high enough to be commercially attractive.

Another object of the present invention is to have a process which minimizes by-products and in particular hydrogenation and hydrosilation products.

Yet another objective of the present invention is to provide novel silanes and siloxanes which heretofore were unable to be synthesized.

Other objectives of the invention will be made more apparent by reference to the detailed specification and examples which follow.

SUMMARY OF THE INVENTION

The present invention provides a novel class of olefinic silanes and siloxanes and a one-step method of preparing such products. The novel olefinic silanes and siloxanes are those prepared via a dehydrocondensation of a complex silicon composition selected from the group consisting of secondary aminosilanes, siloxanes, alkoxysilanes and alkylalkoxysilanes with an olefin in the presence of a rhodium or ruthenium catalyst.

Unexpectedly, it has been found that secondary aminosilanes which show little reactivity for the hydrosilation of olefins, J. Org. Chem. 35, 3879 (1970) react via dehydrocondensation at moderate temperatures with a variety of olefins.

Hindered alkoxysilanes such as tritertbutoxysilane and triisopropoxysilane have also unexpectedly been shown to undergo dehydrocondensation whereas less hindered alkoxysilanes such as trimethoxysilane and triethoxysilane favor hydrosilation under identical conditions, through some dehydrocondensation products have been observed as reported above.

Simple siloxanes such as bis(trimethylsiloxy)methylsilane and heptamethylcyclotetrasiloxane and Si-H fluids also undergo dehydrocondensation. This is unexpected in that siloxanes are well known to undergo rapid hydrosilation.

DETAILED DESCRIPTION OF THE INVENTION

In accordance with the present invention, there is provided a novel method of preparing olefinic silanes and siloxanes. The method comprises the dehydrocondensation of a complex silicon composition selected from the group consisting of secondary aminosilanes, siloxanes, alkoxysilanes and alkylalkoxysilanes with an olefin.

Secondary aminosilanes useful in the dehydrocondensation include those represented by general formula:

$$H-Si(NRR^1)_x(R^2)_{3-x}$$

wherein R, $R^1$ and $R^2$ are individually alkyl or aryl groups containing from 1 to 8 carbon atoms, and wherein x has a value of 1, 2 or 3. Preferably, R, $R^1$ and $R^2$ are either methyl or phenyl and x has a value of 3. These secondary aminosilanes may be purchased commercially or prepared from any of a variety of known techniques, such as described in Eaborn, *Organosilicon Compounds*, Academic Press Inc., New York, 1690, p. 339.

Suitable secondary aminosilanes include, but are not limited to, dimethylaminodimethylsilane, bis(dimethylamino)methylsilane, tris(dimethylamino)silane, dimethylaminomethylethylsilane, diethylaminoethylpropylsilane, diethylaminomethylethylsilane, diphenylaminomethylethylsilane, diphenylaminomethylphenylsilane, dibenzylaminoethylphenylsilane, diphenylaminodimethylsilane, bis(diethylamino)ethylsilane, bis(dimethylamino)ethylsilane, bis(dibenzylamino)methylsilane, tris(diethylamino)silane, tris(piperidino)silane, and tris(dicyclohexylamino)silane. Most preferably the secondary aminosilane is tris(dimethylamino)silane.

Siloxanes useful in the dehydrogenative silylation include those represented by the general formula:

$$R^3{}_{3-a}(H)_aOSiO(R^4{}_2SiO)_y(R^5SiO)_zSi(H)_bR^6{}_{3-b}$$
(with H on the Si in the middle group)

wherein $R^3$, $R^4$, $R^5$ and $R^6$ are individually alkyl or aryl groups containing from 1 to 8 carbon atoms, and a has a value of 0 or 1, b has a value of 0 or 1, y has a value from 0 to 500, z has a value from 0 to 500, and the sum of y+z equals from 0 to 500 with the proviso that if z has a value of 0, a+b must equal at least one. Preferably, the alkyl group is methyl and the aryl group is phenyl. These siloxanes may be purchased commercially or prepared from any of a variety of known techniques, such as described in Eaborn, *Organosilicon Compounds*, Academic Press Inc., New York, 1960, p. 228.

Suitable siloxanes include, but are not limited to, bis(trimethylsilyloxy)methylsilane, 1,1,3,3-tetramethyldisiloxane, and heptamethylcyclotetrasiloxane. Most other siloxanes are generally mixtures of a variety of siloxanes. Preferably the siloxane is such that $R^3$, $R^4$, $R^5$ and $R^6$ are all methyl groups.

Alkoxysilanes and alkylalkoxysilanes useful in the dehydrogenative silylation include those represented by the general formula set forth below:

$$\begin{array}{c} R_v{}^{10} \\ | \\ H-Si(OR^7)_{3-v} \end{array}$$

wherein $R^7$ is an alkyl or aryl group containing from 3 to 10 carbon atoms, $R^{10}$ is an alkyl or aryl group containing from 1 to 8 carbon atoms, and v has a value of 0, 1 or 2. The alkoxysilanes and alkylalkoxysilanes may be purchased commercially or prepared by a variety of known techniques such as are described for example in U.S. Pat. No. 4,395,564. The alkoxysilanes and alkylalkoxysilanes are prepared from secondary or tertiary alcohols. Preferably, v has a value of 0.

Suitable alkoxysilanes and alkylalkoxysilanes include, but are not limited to, triisopropoxysilane, trisecbutoxysilane, tritertbutoxysilane, methyldiisopropoxysilane, dimethyltertbutoxysilane, and methyldisecbutoxysilane.

The olefinic monomers employed in the dehydrocondensation are represented by the general formula:

$$CH_2=C\begin{matrix} R^8 \\ R^9 \end{matrix}$$

wherein $R^8$ and $R^9$ are individually an alkyl, alkenyl, aryl, alkoxy, aryloxy, polyether, alkylsilyl, alkoxysilyl, and aminosilyl groups having from one to fifty carbons and $R^8$ and $R^9$ may also be hydrogen. Preferably, $R^8$ and $R^9$ are hydrogen or one of the above groups having from 1 to 10 carbon atoms. The olefins can be purchased commercially.

Olefinic monomers which are suitable for use in the practice of this invention, are, in general, known compounds and include, but are not limited to, the following: ethylene, propylene, isobutylene, styrene, isoprene, butadiene, allylmethoxytriglycol, and vinylsilanes, including vinyltriethylsilane, vinyltrimethoxysilane, vinyltriethoxysilane, vinyltriisopropoxysilane, vinyltritertbutoxysilane, vinyltris(dimethylamino)silane, vinylmethyldiethoxysilane, vinylmethyldimethoxysilane, vinyldimethylmethoxysilane, and vinyldimethylethoxysilane.

Additionally, other olefinic monomers which are suitable include functional olefins such as allylamine, acrylate and methacrylate esters, and unsaturated ketones.

It is important to note that cyclohexene, internal olefins, i.e. olefins having internal unsaturation ($CH_3-CH=CH-CH_3$), and some olefins which readily isomerize into an internal olefin, do not undergo the dehydrocondensation. It is preferred to employ terminal olefins which do not isomerize into internal olefins.

To obtain primarily (more than 50% and usually more than 75%) of the dehydrocondensation product the reaction takes place in the presence of a rhodium or ruthenium catalyst. The rhodium or ruthenium catalyst may be used neat; on a support such as carbon black or alumina; or in a solvent as a soluble compound of rhodium or ruthenium, i.e., chlorodicarbonylrhodium(I) dimer, dodecarbonyltetrarhodium(O), acetylacetonatodicarbonylrhodium(I). chloro(1,5-cyclooctadiene)rhodium(I) dimer, dodecacarbonyltriruthenium(O) tris(acetylacetonato)ruthenium(III), and complexes of rhodium and ruthenium with phosphines, such as tristriphenylphosphinerhodium(I) chloride, tristriphenylphosphinerhodium(I) carbonylhydride and dichlorotris(triphenylphosphine)ruthenium-(II). The catalysts are available commercially such as from Johnson Mathey. The concentration of the catalyst is normally between 0.000010–0.05 mole % with respect to the silicon composition, it is preferred however to use no more catalyst than required to obtain the necessary reaction due to the significant costs associated with catalysts of this type. However, impurities common in many olefins may necessitate higher concentrations.

The dehydrocondensation should be run at temperatures greater than 40° C. with the optimum temperature being between 100°–200° C. Although the upper temperature limit is not critical, the reaction should be run below the decomposition point of the starting materials or products. The reaction can be run at atmospheric pressure. Increasing or decreasing the pressure would not be expected to generate anything other than one skilled in the art would expect, i.e. alter reaction rates. The reactin may be carried out with or without a solvent. When a solvent is desirable for reasons such as solubility or temperature control, a solvent may be used. Suitable solvents are hydrocarbons such as octane, toluene, xylene or triisopropylbenzene.

The order of the addition of the reactants is not important, although normally, the rhodium or ruthenium catalyst is added to the silicon composition and olefin and then heat is applied. A ratio of 1:2 to 1:5 of the silicon composition to the olefin is preferred. This is done to minimize the reaction of hydrogen generated in the reaction with the olefinic silane or siloxane.

The olefinic silanes or siloxanes which the dehydrocondensation produces are represented by the following general formulae:

A. When the silicon composition is a secondary aminosilane:

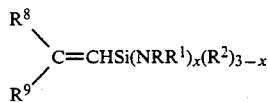

B. When the silicon composition is a siloxane:

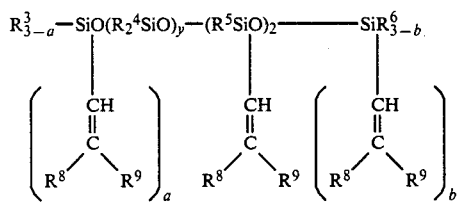

C. When the silicon composition is an alkylalkoxysilane or alkoxysilane:

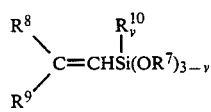

These silanes and siloxanes find utility as coupling agents in a variety of applications including mineral filled composites and fiber glass applications; crosslinking agents for polymers; compounding agents for dental impressions; and encapsulated gels to name but a few.

Whereas the exact scope of the instant invention is set forth in the appended claims, the following specific examples illustrate certain aspects of the present invention and more particularly, point out methods of evaluating the same. However, the examples are set forth for illustration only and are not to be construed as limitations on the present invention except as set forth in the appended claims. All parts and percentages are by weight unless otherwise specified.

DEFINITIONS

Silicon A—Me$_3$SiOSiHMeOSiMe$_3$ ME=methyl
Silicon B—(Me$_2$SiO)$_3$MeSiH(O))
Silicon C—Me$_3$SiO(SiMe$_2$O)$_{15.5}$(SiHMeO)$_{5.5}$SiMe$_3$
Silicon D—Me$_3$SiO(SiMe$_2$O)$_{72}$(SiHMe$_2$O)$_{7.6}$SiMe$_3$
Silicon E—C$_6$H$_{13}$NO$_3$Si(Silatrane)
Silicon F—tris(dimethylamino)silane
Silicon G—HSi(OCH(CH$_3$)$_2$)$_3$
Silicon H—HSi(OC(CH$_3$)$_3$)$_3$
Silicon I—Me$_3$SiO(SiMe$_2$O)$_{13.5}$(SiHMe$_2$O)$_{5.5}$SiMe$_3$
Silicon J—HSi(CH$_2$CH$_3$)$_3$
Silicon K—HSi(OCH$_2$CH$_3$)$_3$
Silicon L—HSi(OCH$_3$)$_3$
Silicon M—HSiCl$_3$
Silicon N—HSiPh$_3$ Ph=phenyl
Silicon O—ClSi(OCH$_3$)$_3$
Olefin A—ethylene
Olefin B—propylene
Olefin C—isobutylene
Olefin D—acetylene
Olefin E—t-butylacetylene
Olefin F—t-butylethylene
Olefin G—butadiene
Olefin H—styrene
Olefin I—methyl acrylate
Olefin J—ethyl acrylate
Olefin K—allylamine
Olefin L—vinyltrisdimethylaminosilane
Olefin M—allyl methoxytriglycol
Olefin N—vinylethylether
Olefin O—1-hexyne
Solvent A—xylene
Solvent B—chlorobenzene
Solvent C—1,3,5-triisopropylbenzene
Solvent D—toluene
Catalyst A—Ru$_3$(CO)$_{12}$
Catalyst B—[RhCl(CO)$_2$]$_2$
Catalyst C—Rh$_4$(CO)$_{12}$
Catalyst D—RuCl$_2$(CO)$_2$(PPh$_3$)$_2$
Catalyst E—Ru(C$_5$H$_7$O$_2$)$_3$
Catalyst F—RuCl$_2$(PPh$_3$)$_3$
Catalyst G—Rh/C
Catalyst H—RhCl(PPh$_3$)$_3$
GC—gas chromatograph
GC/MS—gas chromatograph/mass spectrometry
NMR—nuclear magnetic resonance
psi—pounds per square inch
ppm—parts per million
g—gram
mg—milligram
mol—mole
°C.—degree Centigrade
%—percent

EXAMPLE 1

To a 300 cc high pressure bomb was added 25 g (0.16 mol) tris(dimethylamino)silane, 50 g of xylene and 10 ppm (0.95 mg) of $Rh_2Cl_2CO_4$ as a catalyst. After the bomb was secured in a rocker/heater, the ethylene feed line was attached and the bomb heated to 50° C., at which time the bomb was charged to 1200 psi (0.69 mol) with ethylene. After rocking was initiated, the pressure dropped to 900 psi due to ethylene solubility in the reaction mixture. Heating was continued and the pressure rose to 1450 psi at 148° C., where an exotherm occurred increasing the temperature to 225° C. and the pressure to 1900 psi. The heater was immediately turned off and the reaction cooled. GC and GC/MS analysis showed the product mixture to contain 87.4% vinyltris(dimethylamino)silane and 10.6% ethyltris(dimethylamino)silane.

EXAMPLE 2

The reaction was run as described in Example 1 except that a one to one mole ratio of tris(dimethylamino)silane and ethylene was used. The product mixture after the reaction was complete was shown to contain 20.3% tris(dimethylamino)silane, 23.6% vinyltris(dimethylamino)silane and 51.7% ethyltris(dimethylamino)silane.

EXAMPLE 3

The reaction was run as described in Example 1 except that triisopropoxysilane was used as as the starting silicon composition. After the reaction was complete the product mixture was shown to contain approximately 85% vinyltriisopropoxysilane, 7% ethyltriisopropoxysilane and 3% tetraisopropoxysilane.

EXAMPLE 4

The reaction was run as described in Example 1 except that tritertbutoxysilane was used as the starting silicon composition. The product mixture was shown to contain 96% vinyltritertbutoxysilane and 2% ethyltritertbutoxysilane.

EXAMPLE 5

The reaction was run as described in Example 1 except that triethoxysilane was used as the starting silicon composition. The product mixture was shown to contain 62% vinyltriethoxysilane, 28% ethyltriethoxysilane and 6% tetraethoxysilane.

EXAMPLE 6

The reaction was run as described in Example 1 except that trimethoxysilane was used as the starting silicon composition. The product mixture was shown to contain 12% vinyltrimethoxysilane, 78% ethyltrimethoxysilane and 4% tetramethoxysilane.

EXAMPLE 7

The reaction was run as described in Example 1 except that bis(trimethylsiloxy)methylsilane was used as the starting silicon composition. The product mixture was shown to contain 72% vinylbis(trimethylsiloxy)methylsilane and 25% ethylbis(trimethylsiloxy)methylsilane.

EXAMPLE 8

The reaction was run as described in Example 1 except that heptamethylcyclotetrasiloxane was used as the starting silicon composition. The product mixture was shown to contain 62% vinylheptamethylcyclotetrasiloxane and 36% ethylheptamethylcyclotetrasiloxane.

EXAMPLE 9

The reaction was run as described in Example 1 except that $Me_3SiO(Me_2SiO)_{13.5}(MeSiHO)_{5.5}SiMe_3$ was used as the starting silicon composition. Analysis by $^1H$ NMR showed the product to be

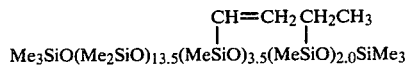

$$Me_3SiO(Me_2SiO)_{13.5}(MeSiO)_{3.5}(MeSiO)_{2.0}SiMe_3$$
with CH=CH$_2$ and CH$_2$CH$_3$ substituents

EXAMPLE 11

The reaction was run as described in Example 1 except 1000 ppm $Ru_3CO_{12}$ was used as the catalyst. The product mixture was shown to contain 57.5% vinyltris(dimethylamino)silane and 40.2% ethyltris(dimethylamino)silane.

EXAMPLE 12

The reaction was run as described in Example 1 except that 10 ppm Rh/C was used as the catalyst. The product mixture contained 80.1% vinyltris(dimethylamino)silane and 9.9% ethyltris(dimethylamino)silane.

EXAMPLE 13

Into a 45 cc Parr bomb was added 1.5 g (0.0093 mol) tris(dimethylamino)silane, 8.5 g xylene and 8 ml (0.1143 mol) propylene and 1000 ppm (3.1 mg) $Ru_3CO_{12}$ as a catalyst. The bomb was then heated in a fluidized sand bath at 235° C. for 5 hours. The reaction mixture was then cooled to room temperature. A $^1H$ and $^{13}CNMR$ showed that product mixture contained 73% 1-tris(dimethylamino)silylprop-1-ene, 9% allyltris(dimethylamino)silane and 8% propyltris(dimethylamino)silane.

EXAMPLE 14

To a 1 liter autoclave, was added 250 g (1.5 mol) tris(dimethylamino)silane, 100 g xylene, 168 g (3.1 mol) 1,3-butadiene and 200 ppm $RhCl(PPh_3)_3$ (0.45 g) as the catalyst. After the autoclave was secured, the reaction was heated to 125° C. for four hours. The reactor was then cooled to room temperature. GC and GC/MS revealed that the major product formed was 1-tris(dimethylamino)silylbuta-1,3-diene in 65% yield. 1-tris(dimethylamino)silylbut-1-ene was also formed in 32% yield.

EXAMPLE 15

To a 45 cc high pressure bomb was added 3.75 g (0.0025 mol) $Me_3SiO(Me_2SiO)_{13.5}(MeSiO)_{5.5}SiMe_3$, 5.26 g (0.05 mol) styrene, 2.0 g xylene and 1000 ppm (8.1 mg) $Ru_3CO_{12}$ as a catalsyt. Phenothiazine (75.6 mg) was also added to help prevent polymerization of the styrene. The bomb was then heated in a fluidized sand bath at 125° C. for 10 hours after which time the reaction was cooled to room temperature. The solvent and excess styrene as well as ethylbenzene formed during the course of the reaction was removed under vacuum. Analysis by $^1HNMR$ showed the product to be

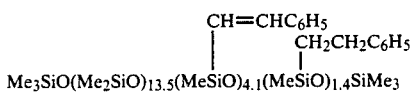

EXAMPLE 16

Into a 45 cc Parr bomb was added 1.5 g (0.007 mol) triisopropoxysilane, 8.5 g triisopropylbenzene, 7 g (0.16 mol) propylene and 1000 ppm (3 mg) $Ru_3CO_{12}$ as a catalyst. The bomb was then heated in a fluidized sand bath at 235° C. for 3 hours. By GC and GC/MS the reaction mixture contained approximately 65% 1-triisopropoxysilylprop-1-ene and 30% propyltriisopropoxysilane.

EXAMPLE 17

Into a 45 cc Parr bomb was added 5 g (0.03 mol) tris(dimethylamino)silane, 1 g xylene, 11.9 g (0.06 mol) vinyltriethoxysilane and 100 ppm $Rh_2Cl_2CO_4$ (1 mg) as the catalyst. The bomb was then placed in a fluidized sand bath at 225° C. for 4 hours. After cooling to room temperature a GC and GC/MS revealed that two products had been formed in a 3 to 1 ratio. The major one was identified to be 1-tris(dimethylamino)silyl-2-triethoxysilylethylene and the minor one 1-tris(dimethylamino)silyl-2-triethyoxysilylethane.

EXAMPLE 18

The reaction was run as described in Example 17 except that vinyltris(dimethylamino)silane was used instead of vinyltriethoxysilane. A single product, 1,2-bis(tris(dimethylamino)silyl)ethylene was formed.

EXAMPLE 19

A one liter, 3-necked flask was equipped with a stirring bar, thermometer, 500 ml addition funnel and reflux condenser topped with a nitrogen inlet tube. The flask was charged with 200.0 g (1.21 mol) tris(dimethylamino)silane, 2.27 g phenothiazine and 200 ppm $Rh_2Cl_2CO_4$ (80 mg) as a catalyst. The solution was heated to 120° C. at which time 228 g (2.24 mol) styrene was added dropwise over a period of two hours. There was an initial exotherm to 150° C. and the temperature was then maintained between 120°–150° C. After the addition was complete the reaction was cooled to room temperature. GC and GC/MS confirmed that a single product, 1-tris(dimethylamino)silyl-2-phenylethylene was formed in greater than 90% yield.

EXAMPLE 20

The reaction was run as described in Example 19 except that tritertbutoxysilane was used as the starting silicon composition. One major product, 1=tritertbutoxysilyl-2-phenylethylene was formed in over 80% yield.

EXAMPLE 21

The reaction was run as described in Example 19 except that triisopropoxysilane was used as the starting silicon composition. Two products were formed in a 3 to 1 ratio. The major one was 1-triisopropoxysilyl-2-phenylethylene and the minor one 1-triisopropoxysilyl-2-phenylethane.

EXAMPLE 22

The reaction was run as described in Example 19 except that triethoxysilane was used as the starting silicon composition. Two products were formed in a 2 to 1 ratio. The major one was 1-triethoxysilyl-2-phenylethane and the minor one was 1-triethoxysilyl-2-phenylethylene.

EXAMPLE 23

Into a 45 cc Parr bomb was added 2.5 g (0.010 mol) tritertbutoxysilane, 4.7 g (0.020 mol) vinyltriisopropoxysilane, 1.0 g xylene and 2000 ppm $Ru_3CO_{12}$ (29 mg) as a catalyst. The reaction was heated to 225° C. for 3 hours in a fluidized sand bath. A single product, 1-tritertbutoxysilyl-2-triisopropoxysilylethylene was formed.

EXAMPLE 24

Into a 45 cc Parr bomb was added 2.5 g (0.012 mol) triisopropoxysilane, 5.7 g (0.024 mol) vinyltriisopropoxysilane, 1.0 xylene and 200 ppm $Ru_3CO_{12}$ (20 mg). The reaction was heated for 4 hours at 225° C. in a fluidized sand bath. A single product, 1,2-bis(triisopropoxysilyl)ethylene was formed.

EXAMPLE 25

Into a 45 cc Parr bomb was added 2.5 g (0.016 mol) tris(dimethylamino)silane, 5.28 g (0.078 mol) isoprene, 1.0 g xylene and 200 ppm $Rh_2Cl_2CO_4$ (2 mg) as a catalyst. The reaction was heated to 200° C. for 5 hours in a fluidized sand bath. GC and GC/MS showed that two products had been formed in a 2 to 1 ratio. The major one was 1-tris(dimethylamino)silyl-3-methylbuta-1,3-diene and the minor one 1-tris(dimethylamino)silyl-3-methylbut-1-ene.

EXAMPLE 26

Into a 45 cc Parr bomb was added 2.5 g (0.02 mol) tritertbutoxysilane, 4.2 g (0.04 mol) styrene, 1.0 g xylene, 30 mg phenothiazine and 2000 ppm $Ru_3CO_{12}$ (20 mg). The reaction was heated in a fluidized sand bath at 175° C. for 5 hours. A single product 1-tritertbutoxysilyl-2-phenylethylene was formed in greater than 90% yield.

EXAMPLE 27

The reaction was run as described in Example 25 except that $Ru_3CO_{12}$ was used as the catalyst. Two products were formed in a 2 to 1 ratio with the major product being 1-tris(dimethylamino)silyl-3-methylbuta-1,3-diene and the minor being 1-tris(dimthylamino)silyl-3-methylbut-1-ene.

EXAMPLE 28

The reaction was run as described in Example 19 except that $RhCl(PPh_3)_3$ was used as the catalyst. A single product 1-tris(dimethylamino)silyl-2-phenylethylene was formed in greater than 90% yield.

EXAMPLE 29

The reaction was run as described in Example 19 except that $Ru_3CO_{12}$ was used as the catalyst. A single product 1-tris(dimethylamino)silyl-2-phenylethylene was formed in over 80% yield.

EXAMPLE 30

Into a 45 cc Parr bomb was added 7.5 g (0.03 mol) tritertbutoxysilane, 7.3 g (0.04 mol) allylmethoxytriglycol, 3.0 g xylene and 1000 ppm $Ru_3CO_{12}$ (16 mg). the reaction was heated to 175° C. for six hours. A single product (tBuO)₃SiCH=CHCH₂(OCH₂CH₂)₃OMe was formed in greater than 90% yield.

EXAMPLE 31

The reaction was run as described in Example 30 except that tris(dimethylamino)silane was used instead of tritertbutoxysilane. A single product (Me₂N)₃SiCH=CHCH₂(OCH₂CH₂)₃OMe was formed in greater than 90% yield.

COMPARATIVE EXAMPLE D

The reaction was run as described in Example 4 except that H₂PtCl₆ was used as the catalyst. No product was formed and only starting materials were isolated.

The following tables set forth dehydrocondensation reactions that were run using a variety of starting materials and reaction conditions. The products were analyzed by GC/MS unless otherwise noted.

| EXAMPLE | 32 | 33 | 34 | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|---|---|
| Olefin | A | A | A | A | A | A | A | B | B | C | F | H | H | J | N | N | A | A |
| Silicon | A | B | C | D | E | A | F | G | F | F | F | I | C | K | F | H | K | L |
| Catalyst | A | A | A | A | A | A | A | A | A | A | A | A | A | A | A | A | B | B |
| Cat. Conc (ppm) | 100 | 100 | 1000 | 100 | 300 | 500 | 3000 | 3300 | 3000 | 3175 | 100 | 1000 | 1000 | 1000 | 1000 | 1000 | 60 | 60 |
| Olefin/Silane Molar Conc | 4/1 | 4/1 | 4/1 | 4/1 | 4/1 | 4/1 | 4/1 | 4/1 | 12/1 | 4/1 | 4/1 | 4/1 | 4/1 | 2/1 | 4/1 | 4/1 | 4/1 | 4/1 |
| Solvent | A | A | A | A | B | A | C | C | A | A | A | A | A | A | A | A | A | A |
| (°C.) Temperature | 225 | 225 | 225 | 225 | 225 | 225 | 235 | 235 | 235 | 225 | 150 | 150 | 125 | 150 | 200 | 175 | 200 | 150 |
| (hours) Time | 13 | 5 | 6 | 10 | 17 | 12 | 4 | 4 | 5 | 19 | 6 | 10 | 10 | 4 | 5 | 4.5 | 3 | 3 |
| % Olefinic Product | 80 | 30 | 30 | 57 | 50 | 40 | 59 | 60 | 82 | 80 | >10 | 53 | 55 | 60 | 20 | 60 | 30 | 20 |

| EXAMPLE | 50 | 51 | 51 | 53 | 54 | 55 | 56 | 57 | 58 | 59 | 60 | 61 | 62 | 63 | 64 | 65 | 66 | 67 |
|---|---|---|---|---|---|---|---|---|---|---|---|---|---|---|---|---|---|---|
| Olefin | A | A | A | A | A | A | A | A | A | A | A | A | A | B | B | F | L | G |
| Silicon | G | H | H | F | F | F | F | F | F | M | N | A | B | K | G | F | F | F |
| Catalyst | B | B | B | B | B | B | B | B | B | B | B | B | B | B | B | B | B | B |
| Cat. Conc (ppm) | 160 | 200 | 50 | 100 | 80 | 60 | 10 | 10 | 10 | 100 | 160 | 50 | 50 | 100 | 100 | 100 | 100 | 333 |
| Olefin/Silane Molar Conc | 4/1 | 4/1 | 4/1 | 4/1 | 2/1 | 4/1 | 2/1 | 4/1 | 4/1 | 7/1 | 3/1 | 4/1 | 4/1 | 4/1 | 4/1 | 4/1 | 4/1 | 4/1 |
| Solvent | A | A | A | A | A | A | A | A | N/A | A | A | A | A | C | C | A | A | A |
| (°C.) Temperature | 235 | 175 | 225 | 150 | 150 | 150 | 150 | 170 | 50 | 200 | 235 | 225 | 225 | 225 | 225 | 150 | 200 | 235 |
| (hours) Time | 2 | 2 | 14 | 1 | — | 0.5 | — | 1 | — | 4 | 11 | 14 | 4 | 0.33 | 3 | 8 | 12 | 18 |
| % Olefinic Product | 95 | 90 | >90 | 89 | 16 | 84 | 89 | 90 | 82 | 80 | 25 | 70 | 70 | 60 | 80 | 30 | 50 | 50 |

| EXAMPLE | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|
| Olefin | H | H | H | H | O | E | I | I | K | K | K | A | A | A | D | L | B | M |
| Silicon | A | I | I | F | G | F | J | G | K | K | K | F | O | F | F | L | G | A |
| Catalyst | B | B | B | B | B | B | C | C | D | E | F | G | G | H | H | H | H | H |
| Cat. Conc (ppm) | 100 | 1000 | 100 | 80 | 200 | 200 | 200 | 200 | 1000 | 1000 | 1000 | 10 | 200 | 60 | 60 | 100 | 100 | 300 |
| Olefin/Silane Molar Conc | 4/1 | 2/1 | 2/1 | 4/1 | 2/1 | 4/1 | 4/1 | 4/1 | 2/1 | 4/1 | 2/1 | 4/1 | 4/1 | 4/1 | 4/1 | 5/1 | 4/1 | 4/1 |
| Solvent | A | A | A | A | A | A | D | D | — | A | A | — | A | C | C | A | — | D |
| (°C.) Temperature | 225 | 150 | 150 | 140 | 200 | 200 | 100 | 90 | 175 | 175 | 175 | 200 | 200 | 25 | 200 | 200 | 225 | 126 |
| (hours) Time | 4 | 10 | 7 | 1 | 12 | 12 | — | — | 4 | — | 4 | 10 | 2.5 | 16 | 3 | 2 | — | 1.5 |
| % Olefinic Product | 60 | 53 | 37 | 95 | 70 | 60 | 60 | 70 | 40 | 50 | 50 | 90 | 30 | 21 | 25 | 20 | 80 | 90 |

COMPARATIVE EXAMPLE A

The reaction was run as described in Example 19 except that H₂PtCl₆ was used as the catalyst. No product was formed and only starting materials were isolated.

COMPARATIVE EXAMPLE B

The reaction was run as described in Example 26 except that H₂PtCl₆ was used as the catalyst. No apparent reaction took place and only the starting materials were isolated.

COMPARATIVE EXAMPLE C

The reaction was run as described in Example 1 except that H₂PtCl₆ was used as the catalyst. No product was formed and only starting materials were isolated.

We claim:

1. A process for the preparation of an olefinic silane or siloxane having at least one unit of the general formula

$$>C=CHSi\equiv$$

said process comprising the reaction of (A) a silicon-containing composition selected from the group consisting of (1) secondary aminosilanes of the general formula

$$H-Si(NRR^1)_x(R^2)_{3-x}$$

wherein R, R¹ and R₂ are individually alkyl or aryl groups containing from 1 to 8 carbon atoms, and wherein X has a value of 1, 2 or 3;

(2) siloxanes of the general formula

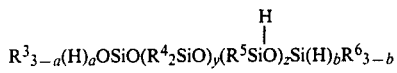

wherein $R^3$, $R^4$, $R^5$ and $R^6$ are individually alkyl or aryl groups containing from 1 to 8 carbon atoms, and a has a value of 0 to 1, b has a value of 0 or 1, y has a value from 0 to 500, z has a value from 0 to 500, and the sum of y+z equals from 0 to 500 with the proviso that if z has a value of 0, a+b must equal at least one; and (3) secondary or tertiary alkylalkoxysilanes or alkoxysilanes of the general formula

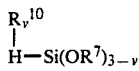

wherein $R^7$ is an alkyl or aryl group containing from 3 to 10 carbon atoms $R^{10}$ is an alkyl or aryl group containing from 1 to 8 carbon atoms and v has a value of 0, 1 or 2, with (B) an olefin of the general formula

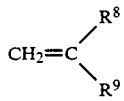

wherein $R^8$ and $R^9$ are individually an alkyl, alkenyl, aryl, alkoxy, aryloxy, polyether, alkylsilyl, alkoxysilyl, and aminosilyl groups having from one to fifty carbons and $R^8$ and $R^9$ may also be hydrogen in the presence of a rhodium or ruthenium catalyst.

2. The process of claim 1 wherein R,R' and $R^2$ are either methyl or phenyl and x has a value of 3.

3. The process of claim 1 wherein the silicon-containing composition is tris(dimethylamino)silane.

4. The process of claim 1 wherein $R^3$, $R^4$, and $R^5$ and $R^6$ are either methyl or phenyl.

5. The process of claim 1 wherein the silicon-containing composition is bis(trimethylsilyloxy)methylsilane.

6. The process of claim 1 wherein $R^7$ is selected from the group consisting of isopropyl, secbutyl and tertbutyl groups.

7. The process of claim 1 wherein v is 0.

8. The process of claim 1 wherein $R^8$ and $R^9$ are hydrogen.

9. The process of claim 1 wherein $R^8$ and $R^9$ have 1 to 10 carbon atoms.

10. The process of claim 1 wherein the catalyst is selected from the group consisting of $Ru_3(CO)_{12}$, $[RhCl(CO)_2]_2$, $Ru_4(CO)_{12}$, $RuCl_2(CO)_2(PPh_3)_2$, $Ru(C_5H_7O_2)_3$, $RuCl(PPh_3)_3$, Rh/C and $RhCl(PPh_3)_3$.

11. The process of claim 1 wherein the catalyst is present in a concentration of between 0.000010 to 0.05 mole percent based on the silicon composition.

12. The process of claim 1 wherein the reaction takes place at 40° C. or greater.

13. The process of claim 1 wherein the reaction takes place between 100°–200° C.

14. The process of claim 1 wherein a solvent is employed.

15. The process of claim 14 wherein the solvent is selected from the group consisting of octane, toluene, xylene, chlorobenzene and 1,3,5-trisopropylbenzene.

16. The process of claim 1 wherein the ratio of the silicon composition to the olefin is 1:2 to 1:5.

17. An olefinic silane or siloxane of the general formula

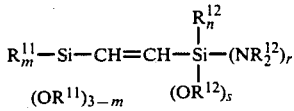

wherein $R^{11}$ and $R^{12}$ are individually hydrogen or an alkyl or aryl group containing from 1 to 8 carbon atoms and $R^{11}$ and $R^{12}$ are different, m, n, r and s individually have a value of 0, 1, 2 or 3 and the sum of n+r+s equals 3.

18. The siloxane of claim 17 wherein m is 3 and $R^{12}$ is selected from the group consisting of methoxy, ethoxy, iso-butoxy, and t-butoxy.

19. The siloxane of claim 17 wherein m is 3, r is 2 or 3, and $R^{12}$ is methyl.

20. The silane of claim 17 wherein m and s are 0, r is 2 or 3 and $R^{12}$ is methyl.

21. An olefinic silane or siloxane of the general formula

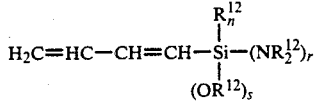

wherein $R^{11}$ is hydrogen or an alkyl or aryl group containing from 1 to 8 carbon atoms, n, r and s individually have a value of 0, 1, 2, or 3 and the sum of n+r+s equals 3.

* * * * *